US00PP13432P2

(12) United States Plant Patent
Tristram

(10) Patent No.: US PP13,432 P2
(45) Date of Patent: Dec. 31, 2002

(54) ERYSIMUM PLANT NAMED 'WALFRASUN'

(76) Inventor: David Ralph Tristram, Old Rectory, Arundel, Binsted, W. Sussex, BN18 0LL (GB)

( * ) Notice: Subject to any disclaimer, the term of this patent is extended or adjusted under 35 U.S.C. 154(b) by 0 days.

(21) Appl. No.: 10/013,267

(22) Filed: Dec. 10, 2001

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—W C Haas
(74) *Attorney, Agent, or Firm*—Mark P. Bourgeois

(57) ABSTRACT

A new cultivar of Erysimum named 'Walfrasun' that is characterized by a large compact, bushy habit, silver-green leaves, chocolate-purple buds and deep-yellow flowers that are strongly sweet in fragrance. In combination these traits set 'Walfrasun' apart from all other existing varieties of Erysimum known to the inventor.

4 Drawing Sheets

BOTANICAL CLASSIFICATION

Erysimum cultivar Walfrasun.

BACKGROUND OF THE INVENTION

The present invention relates to a new and distinct cultivar of perennial wall flower that is grown as an ornamental for its compact, bushy habit and fragrant yellow flower spikes that increase in height as the plant matures. The new cultivar is known botanically as Erysimum and will be referred to hereinafter by the cultivar name 'Walfrasun'.

'Walfrasun' originated in a cultivated area of West Sussex, England. In 1993 a few seeds were produced on an open pollinated plant of Erysimum 'Bredon' (not patented). These seeds were sown by the inventor. One seed germinated, producing a seedling that flowered in 1994. The inventor observed the seedling during a number of months in 1994 and selected it in the same year as 'Walfrasun'.

'Walfrasun' does not set seed and is presumed to be sterile. In addition to being sterile, 'Walfrasun'was selected for its large dimensions, large deep-yellow flowers, strong, sweet scented flowers and buds that are chocolate-purple in color. 'Walfrasun' is a perennial suitable for planting in full sun or partial shade. 'Walfrasun' is closest in comparison to Erysimum 'Bredon' and is distinguishable from 'Bredon' primarily by its vigor, its more silver foliage, its larger mature flower spikes, its deeper chocolate-purple buds, its large deep-yellow flowers that exhibit a strong and sweet fragrance and its absence of seed.

The first asexual reproduction of 'Walfrasun' was conducted by the inventor in 1995 in a cultivated area of West Sussex, England. The method used for asexual propagation was vegetative cuttings. The characteristics of the new cultivar have been determined stable and are reproduced true to type in successive generations.

SUMMARY OF THE INVENTION

The following traits have been repeatedly observed and represent the characteristics of the new cultivar. These traits in combination distinguish 'Walfrasun' from all other commercial varieties known to the inventor. 'Walfrasun' has not been tested under all possible conditions and phenotypic differences may be observed with variations in enviromental, climatic and cultural conditions.

1. Erysimum 'Walfrasun' exhibits a compact bushy habit.
2. Erysimum 'Walfrasun' exhibits leaves with a silver sheen.
3. Erysimum 'Walfrasun' exhibits large deep-yellow flower spikes that increase in height as the plant matures.
4. Erysimum 'Walfrasun' exhibits strong, sweet scented flowers.
5. Erysimum 'Walfrasun' exhibits buds that are chocolate-purple in color.
6. Erysimum 'Walfrasun' does not set seed and is presumed to be sterile.
7. Erysimum 'Walfrasun' is 40–50 cm. in height and 40–60 cm. in width at maturity.
8. Erysimum 'Walfrasun' is hardy to USDA Zones 7–10.

BRIEF DESCRIPTION OF THE DRAWINGS

The accompanying drawings illustate the distinguishing traits of the new Erysimum cultivar named 'Walfrasun'.

The first drawing illustrates an entire plant from a side perspective.

The second drawing shows a close-up view of the flowers.

The first and second drawings show plants grown in three-gallon containers out-of-doors in May in Sussex, England.

The third and fourth drawings show comparisons of 'Walfrasun'with its parent 'Bredon' in Sussex, England.

The third drawing shows a 4-month old plant of each variety in October, illustrating the more silver foliage and greater vigor of 'Walfrasun'.

The fourth drawing shows 12-month old plants of each variety in September, illustrating a typical flower spike of each variety at the end of the flowering period to illustrate the longer spikes of 'Walfrasun' and its wider spacing between the spent flower positions. All drawings were made using conventional photographic techniques and although colors may appear different from actual colors due to light reflectance they are as accurate as possible by conventional photography.

BOTANICAL DESCRIPTION OF THE PLANT

The following is a detailed description of 'Walfrasun' as grown in three-gallon containers out-of-doors for 2.5 years in Sussex, England. The color determinations are in accordance with The R.H.S. Colour Chart of The Royal Horticultural Society, London, England, except where general color terms of ordinary dictionary significance are used. Growing conditions, diseases and pests are similar to that of other Erysimum.

Botanical classification: Erysimum 'Walfrasun'.
Commercial classification: Perennial.
Common name: Wall flower.
Use: Ornamental for container or landscape.
Cultural requirements: Plant in full sun or partial shade and any free-draining soil.
Parentage:
*Female parent*.—Erysimum 'Bredon'.
*Male parent*.—Unknown Erysimum cultivar.
Plant description:
*Bloom period*.—Main period of bloom is April to July. Some blooming continues until October.
*Plant habit*.—Compact and bushy.
*Vigor*.—Vigorous.
*Height*.—40–50 cm. in height.
*Width*.—40–60 cm. in width.
*Hardiness*.—USDA Zones 7–10.
*Root system*.—Fine.
*Propagation*.—Propagation is accomplished using soft cuttings at 20° Centigrade base temperature.
*Time to develop roots*.—Roots are produced within 3 weeks.
*Crop time*.—Seven months are required to produce a finished one-gallon container from a rooted cutting.
Stem:
*Shape*.—Round.
*Stem color*.—189B.
*Stem length*.—30 cm.
*Stem surface*.—Pubescent.
*Basal branch dimensions*.—1.50–2.50 cm. in diameter.
*Basal branch surface*.—Furfuraceous.
*Basal branch color*.—197A.
*Branching*.—Basal branching.
*Internode length*.—0.3–2.0 cm. between nodes.
Foliage:
*Type*.—Evergreen.
*Shape*.—Lanceolate.
*Division*.—Simple.
*Apex*.—Acute.
*Base*.—Attenuate.
*Venation*.—Pinnate with central vein depressed on upper surface and protruding on lower surface.
*Vein color* (*upper and lower surfaces*).—189A.
*Margins*.—Entire with occasional small teeth.
*Arrangement*.—Alternate and spirally up stem.
*Attachment*.—Sessile.
*Surface* (*adaxial and abaxial*).—Slightly pubescent.
*Leaf dimensions*.—6–12 cm. in length and 16–20 mm. in width.
*Leaf color* (*upper surface*).—189A with sheen of 122A.
*Leaf color* (*lower surface*).—189A with sheen of 122A.
*Fragrance*.—Absent.
Flowers:
*Type*.—Inflorescence.
*Shape*.—Rotate.
*Individual flower dimensions*.—20–27 mm. in width and 10–12 mm. in height.
*Persistent or self-cleaning*.—Self-cleaning.
*Aspect*.—Erect and facing upward.
*Quantity*.—50–120 flowers that open over a 4-month period.
*Rachis dimensions* (*at maturity*).—20–30 cm. in length and 2 mm. in diameter with 4–5 flower positions per cm. at 5 cm. from the end of the inflorescence.
*Type of inflorescence*.—Bractless racemes.
*Throat depth*.—7–10 mm. in depth.
*Fragrance*.—Strong, sweet scent.
*Sexuality*.—Bisexual.
*Bud shape*.—Ovate and slightly flattened.
*Bud dimensions*.—2–3 mm. in width, 4–5 mm. in depth and 8–10 mm. in height.
*Bud color*.—166A.
*Flower color*.—Flower color newly opened is 14A, later fading to 12A.
*Petals*.—Four in number.
*Fused or unfused*.—Unfused.
*Petal dimensions*.—8–12 mm. in length and 8–14 mm. in width.
*Petal shape*.—Orbicular.
*Petal margin*.—Entire.
*Petal surface*.—Glabrous.
*Calyx dimensions*.—3–4 mm. in width, 5–7 mm. in depth and 9–11 mm. in height.
*Calyx color*.—166A.
*Calyx surface*.—Pubescent.
*Sepals*.—Four in number.
*Sepals fused or unfused*.—Unfused.
*Sepal margin*.—Entire.
*Sepal shape*.—Lanceolate.
*Sepal apex*.—Acute.
*Sepal dimensions*.—9 mm. in length and 2 mm. in width.
*Peduncle dimensions*.—4–6 mm. in length and 1 mm. in diameter.
*Peduncle color*.—138B.
*Peduncle surface*.—Pubescent.
Reproductive organs:
*Stamens*.—Six in number.
*Stamen color*.—8C.
*Stamen dimensions*.—5–8 mm. in length and 0.5–1.0 mm. in diameter.
*Anther color*.—11B.
*Anther shape*.—Linear.
*Anther dimensions*.—0.5 mm. in width and 2 mm. in length.
*Pollen color*.—11B.
*Amount of pollen*.—Small amount.
*Pistil*.—One.
*Pistil length*.—3 mm. in length.
*Pistil shape*.—Club-shaped.
*Pistil color*.—151A.
*Stigma shape*.—Bifid.
*Stigma color*.—151A.
*Stigma dimensions*.—1 mm. in width, 2 mm. in depth and 1 mm. in height.
*Style color*.—152D.
*Style length*.—2 mm. in length.
*Ovary position*.—Superior.
*Ovary color*.—191C.
*Ovary shape*.—Long, narrow and cylindrical.

*Ovary dimensions*.—7 mm. in height and 2 mm. in diameter.

Seed production: 'Walfrasun' does not set seed and is presumed to be sterile.

I claim:

1. A new and distinct cultivar of Erysimum plant named 'Walfrasun' as described and illustrated herein.

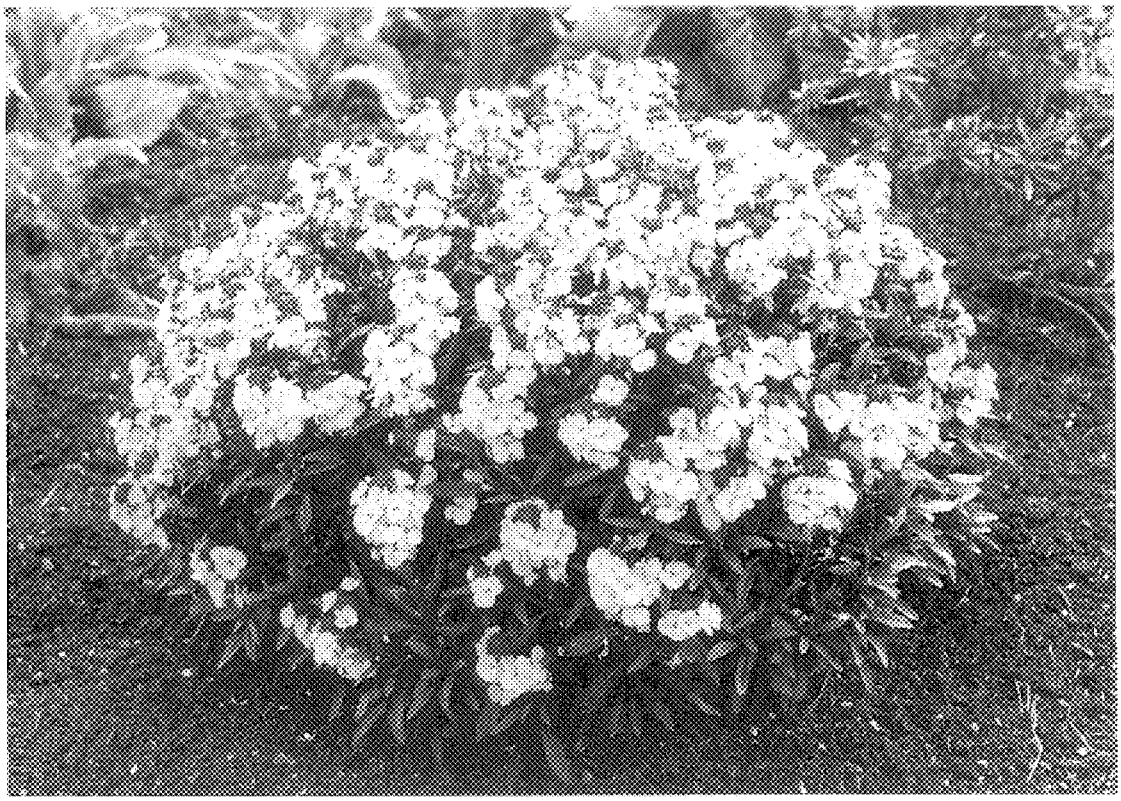

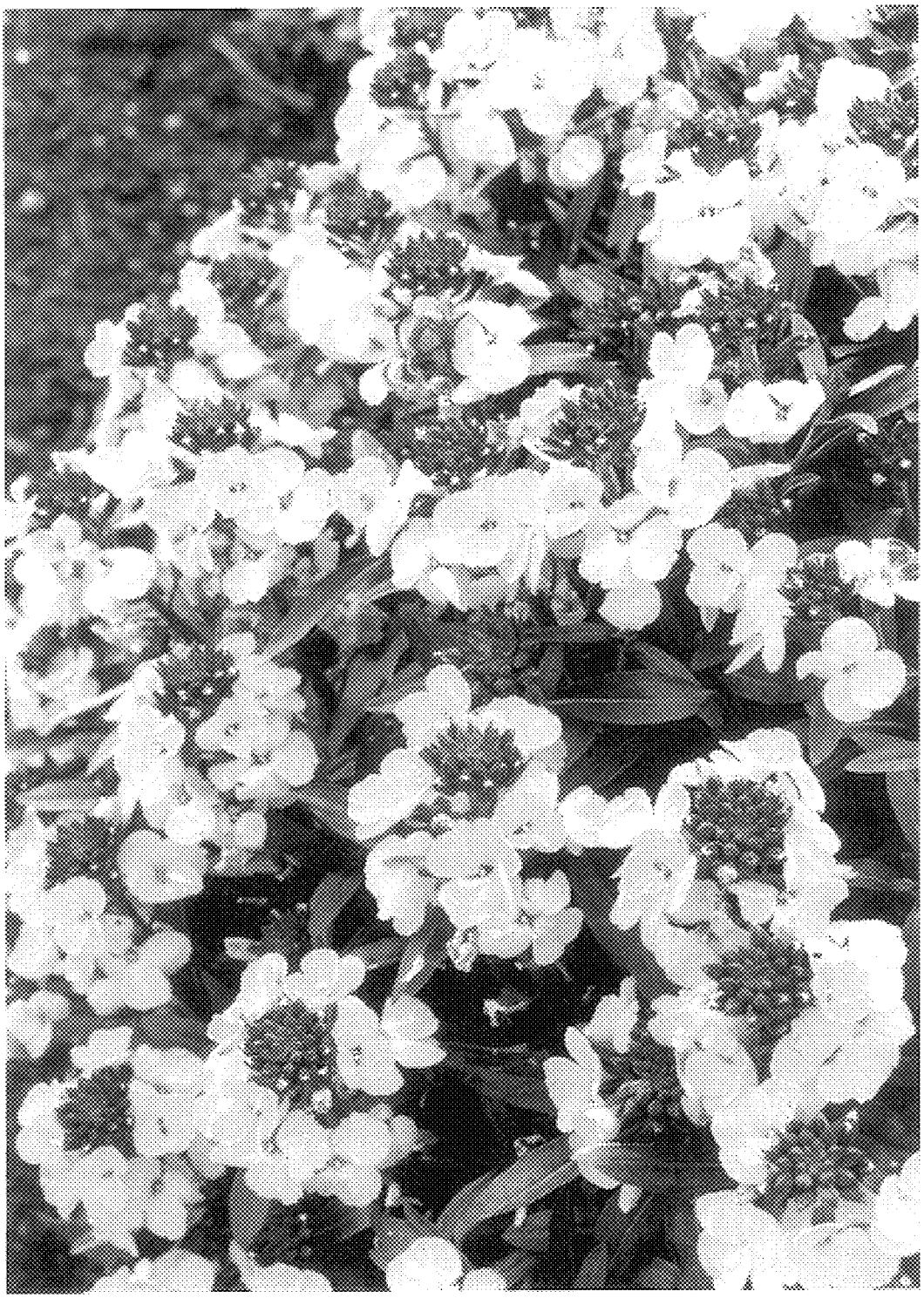

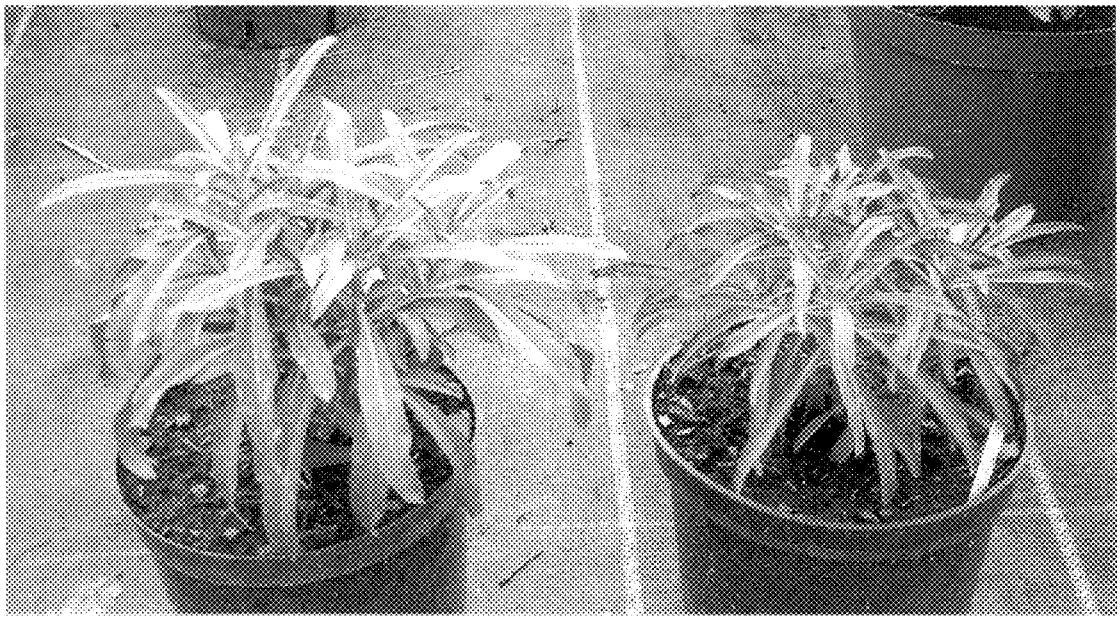

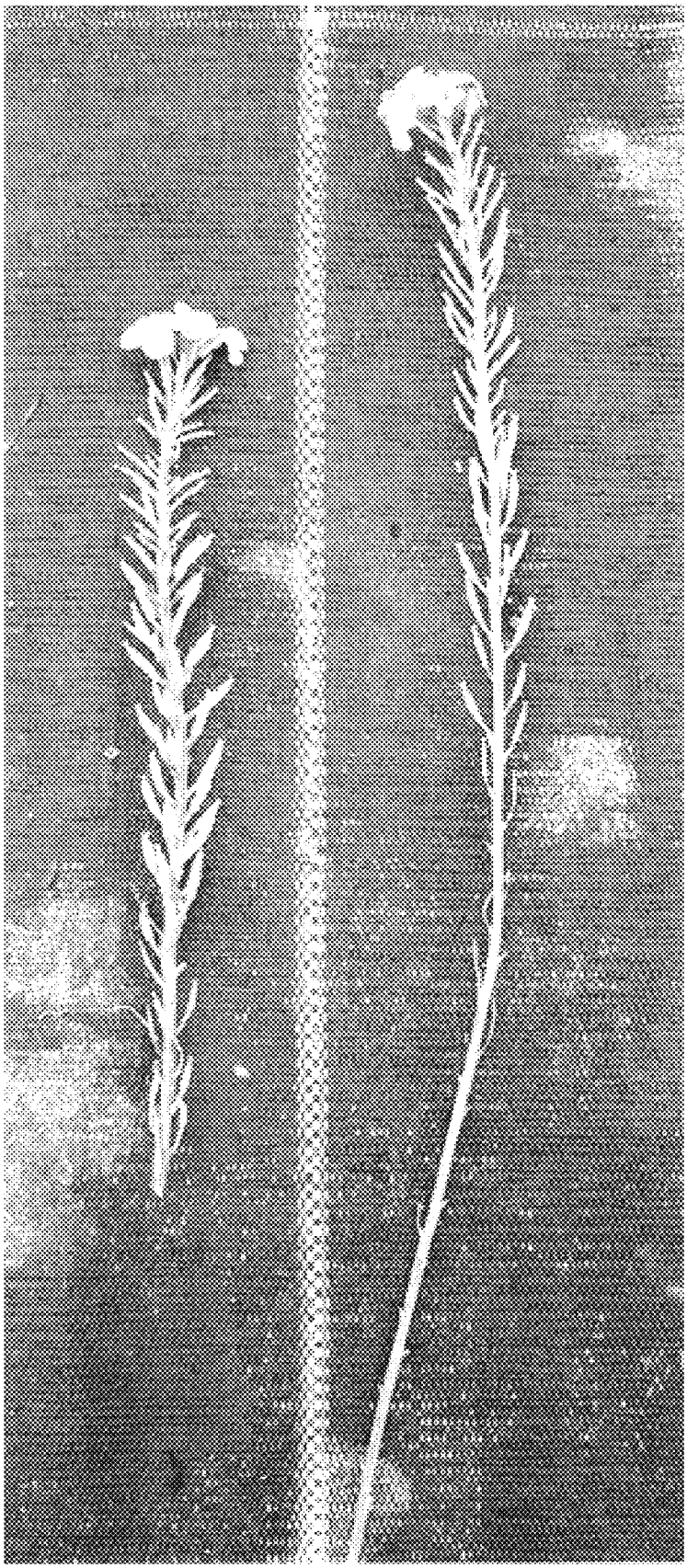

* * * * *